United States Patent [19]

Hashiue et al.

[11] Patent Number: 4,650,556
[45] Date of Patent: Mar. 17, 1987

[54] MEANS FOR ELECTROPHORESIS SHOWING REDUCED SMILING EFFECT

[75] Inventors: Masakazu Hashiue, Kaisei; Masashi Ogawa; Daijiro Nishio, both of Asaka, all of Japan

[73] Assignee: Fuji Photo Film Co., Ltd., Kanagawa, Japan

[21] Appl. No.: 710,131

[22] Filed: Mar. 11, 1985

[30] Foreign Application Priority Data

Mar. 12, 1984 [JP] Japan ................................. 59-47557
Apr. 20, 1984 [JP] Japan ................................. 59-79613

[51] Int. Cl.⁴ ........................ G01N 27/26; G01N 27/28
[52] U.S. Cl. ............................... 204/182.7; 204/180.1; 204/182.8
[58] Field of Search ............. 204/299 R, 182.7, 182.8, 204/180.1, 301

[56] References Cited

U.S. PATENT DOCUMENTS

| | | | |
|---|---|---|---|
| 3,951,776 | 4/1976 | Eibl et al. | 204/299 R |
| 4,194,963 | 3/1980 | Denckla | 204/299 R |
| 4,309,268 | 1/1982 | Richman | 204/301 |
| 4,414,073 | 11/1983 | Iwata et al. | 204/299 R |
| 4,415,418 | 11/1983 | Turre et al. | 204/299 R X |

Primary Examiner—John F. Niebling
Assistant Examiner—B. J. Boggs, Jr.
Attorney, Agent, or Firm—Toren, McGeady and Goldberg

[57] ABSTRACT

A medium for electrophoresis which is substantially free from smiling effect or is reduced in the smiling effect, in which both side portions along the direction of electrophoresis are made thicker than the center portion. A support preferably employed for the preparation of the medium is also disclosed.

6 Claims, 17 Drawing Figures

MEANS FOR ELECTROPHORESIS SHOWING REDUCED SMILING EFFECT

BACKGROUND OF THE INVENTION

1. Field of the Invention

The invention relates to a medium for electrophoresis and a support for the preparation thereof.

2. Description of Prior Arts

There has been heretofore known electrophoresis for separating proteins, decomposition products of protein, nucleic acids, and decomposition products of nucleic acid by means of a sheet-type medium such as a gel membrane or filter paper impregnated with a buffer solution, which is based on phenomenon that the charged particles of said substances migrate under the influence of the electric field. Particularly, electrophoresis has been advantageously performed for the purposes of separation and identification of biopolymers as mentioned above.

In the genetic engineering field which has been paid more attention recently, the electrophoresis is regarded inevitable for determination of base sequence of nucleic acids such as DNA. Electrophoresis performed for the above purpose generally includes a process of causing a plurality of mixtures of radiactively labeled DNA or mixtures of base specifically cleaved products of DNA to migrate in parallel along the longitudinal direction of a medium for electrophoresis. The base sequence is determined by comparing a plurality of thus obtained electrophoretic patterns (an aggregate of zones (or bands) formed in a medium by electrophoresis.) This process is based on a principle that the base specifically cleaved products having the same molecular weight would migrate to the same positions as each other, as far as the starting positions for the electrophoresis procedure is the same as each other.

In the practical runs of electrophoresis, however, the substances having the same molecular weight are apt to migrate to the different positions. Therefore, the respective migration distances of the substances are not equal. In other words, the migration rate of charged substance is generally apt to be lower at the both side portions than at the central portion, and therefore, the pattern of electrophoresis after a lapse of certain time shows that the migration distance is shorter at both side portions than at the center portion as shown in FIG. 1. FIG. 1 is a schematic view of electrophoresis patterns of zones 13 and 13' obtained by electrophoresis starting from a starting point 12 on a medium 11. This phemomenon is called "smiling effect". The smiling effect reduces accuracy of the result obtained by the determination process of base sequence of DNA which involves a procedure of comparing a plurality of rows (i.e., lane) of electrophoresis.

The smiling effect is mainly caused by difference of temperature between the center portion and side portion which is brought about by escape due to radiation of heat (Joule's heat) generated in the medium from the side edge portions. In more detail, while at the center portion of the medium the generated Joule's heat radiates from the upper and bottom surfaces, at the side edge portions Joule's heat radiates not only from the upper and bottom surfaces but also from the side edge portion. In order to compensate the heat radiation, heat moves in the lateral (width) direction. The heat radiation can be easily compensated at the center portion of a medium because heat comes in from both sides. On the other hand, heat radiation cannot be fully compensated at the both sides because heat comes in from only one side. For these reasons, temperature at the side portions is apt to be lower than that at the center portion. In order to prevent generation of the smiling effect, a heat radiation plate is generally provided all over the surface of an electrophoresis medium so as to reduce the difference of temperature. However, it is difficult to sufficiently prevent smiling effect by the above conventional method. Moreover, it is not easy to provide the heat radiation plate to the electrophoresis medium.

SUMMARY OF THE INVENTION

An object of the present invention is to provide a medium for electrophoresis capable of preventing or reducing the smiling effect which is apt to be generated in the procedure of electrophoresis wherein a plurality of electrophoresis rows are to be formed on one medium.

In one aspect, the present invention resides in a medium for electrophoresis characterized in that both side portions along the direction of electrophoresis are made thicker than the center portion.

In another aspect, the present invention resides in a sheet-type support for the preparation of a medium for electrophoresis having side portions along the direction of electrophoresis being made thicker than the center portion, characterized in that the section thereof taken along the width direction has on either side a concave portion.

In the specification, the term "both side portions of medium" means both side portions outside of the effective area of the medium, that is, side portions outside of the the entire area where a plurality of electrophoresis rows are formed. Accordingly, said term does not alwvays mean both side edge portions of the medium.

DETAILED DESCRIPTION OF THE INVENTION

The present invention will be described in detail with reference to the attached drawings.

As mentioned above, the medium for electrophoresis according to the present invention is characterized in that both side portions along the direction of electrophoresis (i.e., electrophoresis path) are made thicker than the center portion. In the medium of the invention formulated as above, a sufficient amount of Joule's heat is produced on the side portions of the medium for compensating the radiation of heat therefrom. Moreover, since the total vacant area for allowing the migration of the charged products increases on the side portions of the medium of the invention, the migration rate on the side portions increases. Accordingly, the smiling effect can be prevented or at least can be effectively reduced in an electrophoresis procedure using the medium of the present invention.

Figure 2:
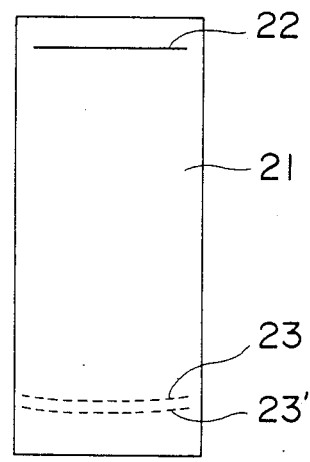
FIG. 2 is a schematic view of a pattern of electrophoresis appearing on a medium for electrophoresis according to the present invention.
Figure 2:
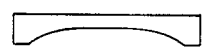

A medium for electrophoresis according to the present invention can have the shape as illustrated in FIG. 2. The medium 21 in FIG. 2 has a shape in which the length and width are substantially the same as those of the conventional medium, but the section taken along the width direction has an arc-shaped concave possessing a straight-lined bottom portion therein on the upper side corresponding to the upper surface of the medium, whereby both side portions along the electrophoresis path are made thicker than the center portion.

In an electrophoresis procedure, the medium 21 of FIG. 2 is water-tightly sandwiched between a pair of support members such as glass plates or plastic films. One (or both) of the support members has on one surface a shape capable of compensating the characteristic shape of the surface of the medium. Thus, the support member generally has a section (taken along the width direction) possessing either side a concave portion. The support can have a section (taken along the width direction) possessing an arc-shaped convex with a straight-lined top portion therein.

The lower end portion of the medium 21 is immersed in a buffer solution in contact with an electrode in accordance with a known method, and the upper end portion thereof is brought into contact with a buffer solution in contact with an electrode in accordance with a known method. Then, the electrophoresis starts. The charged substances starting from the migration starting point 22 show a certain migration pattern (i.e., electrophoresis pattern) on the medium 21 after a given period of time. The migration pattern given on the medium 21 of the invention has a straight-lined pattern or a nearly straight-lined pattern as illustrated in FIG. 2 by the numeral 23, 23'. Thus, the disadvantageous smiling effect is prevented or at least is reduced.

Figure 3:
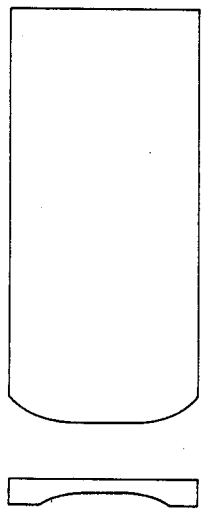
FIG. 3 is a schamatic view showing an example of the medium for electrophoresis according to the invention.

The lower end of the medium of the present invention may have the straight-lined edge as illustrated in FIG. 2, and may have a protruding arc shape possessing a straight-lined center portion as illustrated in FIG. 3.

Figure 4A:
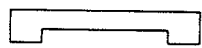
FIGS. 4a, 4b, 4c, 4d and 4e are schematic views showing other examples of the shape (the shapes are given as vertical views seen from the end in the electrophoresis direction) of the medium for electrophoresis of the invention.
Figure 4B:
Figure 4C:
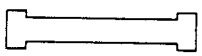
Figure 4D:
Figure 4E:

The section of the medium of the invention taken along the width direction may have a concave shape with a straight-lined center portion therein as illustrated in FIGS. 4a, 4b and 4c. Thus, the change of thickness of the medium may be continuous or stepwise. In the case that the width of the medium is small, the section of the medium may have a simple arc shape to provide a thicker central portion, as illustrated in FIG. 4d. The shape of FIG. 4e may be also applicable.

Figure 5:
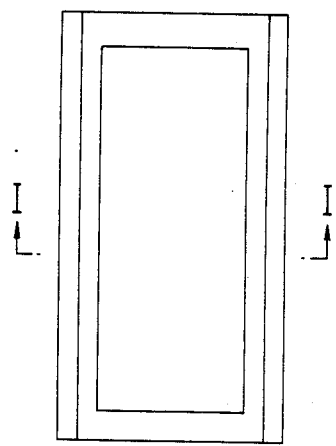
FIG. 5 is a schematic view showing another example of the medium in which the vacant area enclosed with the hatched portions indicates a section of the medium, the hatched portion indicating a section of a support for the medium.
Figure 5:
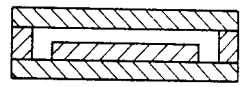

It is not required that the section of the medium of the invention has the same shape throughout along the longitudinal direction (or along the electrophoreis path). For instance, the upper and lower end portions of the medium may have a simple rectangular section similar to that of the conventional medium and the characteristic shape of the invention may be given to the portion between the above-mentioned end portions, as illustrated in FIG. 5.

There is no limitation on nature of the medium for electrophoresis employable in the invention, and any of known media such as a filter paper, cellulose acetate membrane, starch gel membrane and polyacrylamide gel membrane can be employed. The polyacrylamide gel membrane is particularly preferred.

The medium of the invention having thicker side portions can be prepared by processing a conventional medium for electrophoresis in an appropriate shape. However, the medium generally is very thin, and should be processed very carefully.

In the case that the medium is a gel membrane such as a polyacrylamide gel membrane, such gel membrane can be prepared by introducing a gel-forming solution into a mold formed by placing a suitably shaped frame as well as a thinner spacer (the latter serves to produce the thinner central portion on the resulting gel membrane) on a surface of a support such as a glass plate and plastic film or other plates and then hardening the solution.

In preparing a medium for electrophoresis of the invention, the desired difference of thickness can be experimentally determined.

Initially, a conventional rectangular medium is formed on a sheet-type support. Subseuently, the process of electrophoresis is performed on the medium under the predetermined conditions. Then, the degree of the smiling effect, that is, the difference of the migration distance between at both side portions and at center portion is measured on the obtained electrophoresis patterns. On the basis of this measurement, the desired difference in thickness between the central portion and the side portions is assumed, and the same medium except that the assumed difference is applied thereto is prepared. The electrophoresis under the same conditions is then performed on the newly prepared medium. If the pattern of electrophoresis on this medium is satisfactory, the assumed difference is adopted and a medium having the same section is used in practice as the improved version. If the pattern of electrophoresis is not satisfactory, the trial to ascertain an appropriate shape is repeated.

As described above, the medium of the invention is preferably prepared using a specifically shaped support.

Figure 6:
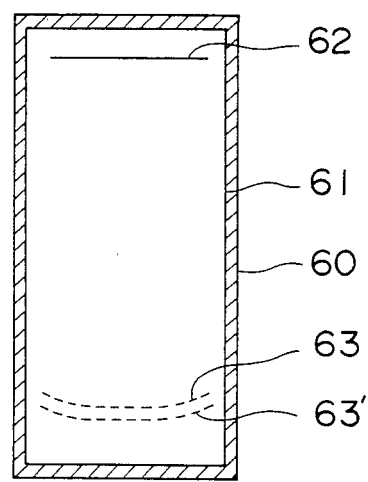
FIG. 6 is a schematic view of a conventional medium for electrophoresis showing a smiling effect thereon, the medium being arranged on a conventional sheet-type support.
Figure 6:
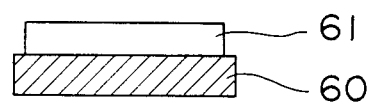
Figure 7:
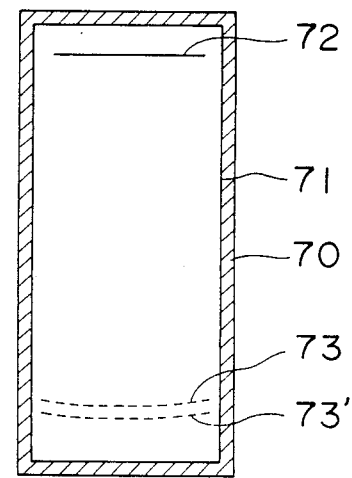
FIG. 7 is a schematic view of a medium of the invention showing an improved pattern of electrophoresis thereon, which is arranged on a sheet-type support of the invention.
Figure 7:
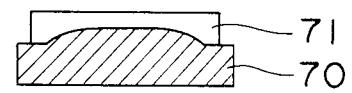
Figure 8A:
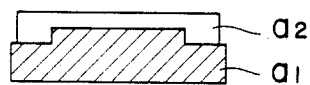
FIGS. 8a, 8b, 8c, 8d and 8e are schematic views showing other examples of the shape (the shapes are given as vertical views seen from the end in the electrophoresis direction) of the support of the invention in combination with a medium for electrophoresis of the invention.
Figure 8B:
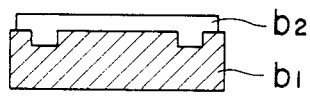
Figure 8C:
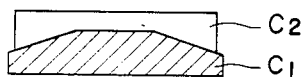
Figure 8D:
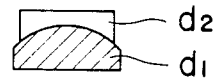
Figure 8E:
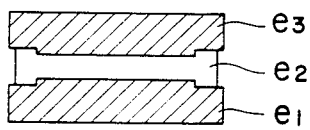
Figure 9:
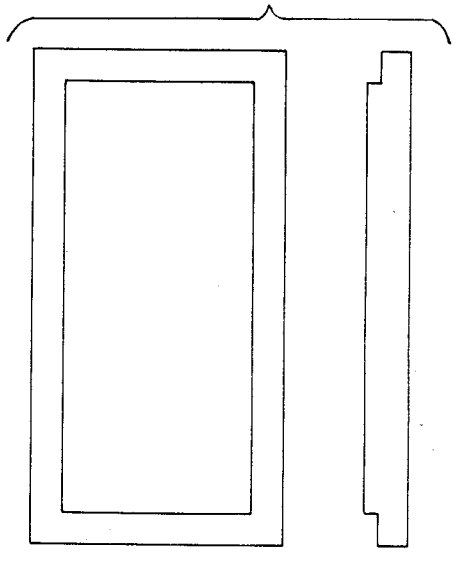
FIG. 9 is a schematic view showing another example of the support of the invention.
Figure 9:
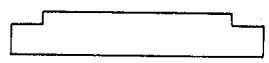

In FIG. 6, the conventional support (i.e., mold) 60 in combination with the electrophoresis medium 61 is illustrated. As stated hereinbefore, the electrophoresis pattern generally is produced under the smiling effect, see 63, 63'. The starting point is indicated by 62. In the case that the support 70 is shaped to have a thicker central portion as illustrated in FIG. 7, the medium 71 can be easily formed on the support 70 to have thicker side portions, as illustrated in FIG. 7. The resulting medium satisfies the condition of the invention and provides an improved electrophoresis pattern 73, 73'. The starting point is indicated by 72.

The appropriate support may have a section of any shape as far as the section has a central thinner portion therein. For instance, any of shapes illustrated in FIGS. 8a, 8b, 8c, 8d and 8e is applicable to the section of support. In FIGS. 8a to 8e, the variations of the section of the support are indicated by the symbols $a_1$, $b_1$, $c_1$, $d_1$, $e_1$, and $e_3$, which are combined respectively with mediums of the invention indicated by the symbols $a_2$, $b_2$, $c_2$, $d_2$, and $e_2$.

FIG. 8 shows still another variation of the support which essentially corresponds to the medium illustrated in FIG. 5.

The support can be made of glass or any plastic material such as acryl resin and polyolefin resin.

The present invention will now be described in more detail with reference to example and comparison example.

COMPARISON EXAMPLE 1

Surfaces of a couple of colorless, transparent sheets of polyethylene terephthalate (length: 37 cm, width: 20 cm, thickness: 180 μm) were treated with glow discharge treatment (200 V, 1.0 A) to prepare a pair of supports.

A tape of polyethylene terephthalate provided with adhesive layers on the both surfaces (width: 10 mm, thickness including the addhesive layers: 0.5 mm) was arranged on the both side portions of the hydrophilic surface of the above support member. Thus arranged tape served as a spacer.

Independently, a gel-forming solution was prepared by adding a polymerization initiator consisting of 1.3 ml. of ammonium peroxodisulfate (5 wt.% aqueous solution) and 33 μl. of TEMED (N,N,N',N'-tetramethylethylenediamine) into 100 ml. of an aqueous solution consisting of 9.5 g. of acrylamide, 0.5 g. of BIS (i.e., N,N'-methylenebisacrylamide), 0.3 g. of agarose (gelation temperature: 36° C., low electroendosmosis type), 2.5 g. of polyacrylamide, 3.58 g. of disodium hydrogen phosphate 12 hydrates, 0.33 g. of sodium dihydrogen phosphate 2 hydrates, and 0.10 g. of SDS (sodium dodecyl sulfate). The gel-forming solution was introduced into the space formed by the spacer and the support and then gelation was performed to obtain a polyacrylamide gel membrane having thickness of 0.5 mm. Then, 17 slots for introducing sample were formed at equal spaces on one end portion of the gel membrane. The gel membrane was covered with the other support via the spacer so as to prepare a medium for electrophoresis.

Electrophoresis of bromophenol blue [CAS Registry No. 115-39-9] was performed according to the vertical method for 3 hours at 1000 V. of applied voltage (DC) by means of an apparatus for electrophoresis manufactured by Marisol Corp., using the above medium and a buffer solution consisting of 1.05 g. of tris(hydroxymethyl)aminomethane, 0.55 g. of boric acid, 93 mg. of EDTA.2Na and water to make it 100 ml.

Figure 1:
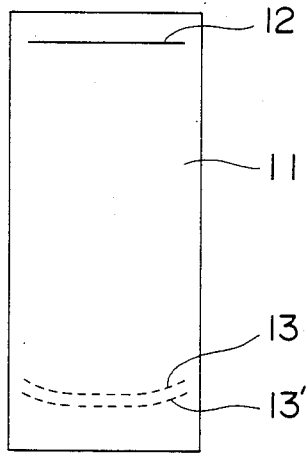
FIG. 1 is a schematic view showing a smiling effect appearing on a conventional medium for electrophoresis.
Figure 1:
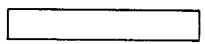

Smiling effect appeared on the electrophoresis pattern as shown in FIG. 1. The migration distance at the center portion was different from that at the side portions by 3 cm.

EXAMPLE 1

Surfaces of a couple of colorless, transparent sheets of polyethylene terephthalate were treated to be made hydrophilic in the same manner as in Comparison Example 1 to obtain a pair of supports (length: 37 cm, width: 20 cm, thickness: 180 μm).

A tape of polyethylene terephthalate provided with addhesive layers on both surfaces (width: 10 mm, thickness including the addhesive layers: 0.5 mm) was placed on the both side portions of the hydrophilic surface of one of the above sheet members. Subsequently, a colorless, transparent polyethylene terephthalate spacer sheet (length: 27 cm, width: 14 cm, thickness 180 μm), the surface of which had been made hydrophilic in the same manner as in Comparison Example 1 was fixed by adhesion to the central area of the support sheet, so as to give a support sheet carrying a mold with an island at the center portion as in FIG. 5.

A polyacrylamide gel membrane was formed on the support in the same manner as in Comparison Example 1. Then, 17 slots for sample introduction were formed at equal spaces on the non-cut end portion of the gel membrane. The gel membrane was covered with the other support to prepare a medium for electrophoresis as in FIG. 5.

Electrophoresis of bromophenol blue was performed for 3 hours under the same conditions as Comparison Example 1 except that the above medium was employed.

The pattern of electrophoresis was substantially linear as shown in FIG. 2 and the smiling effect was so small as to be neglected.

We claim:

1. In a process for electrophoresis using a rectangular means comprising a support and an electrophoresis medium layer provided on the support in which the thickness of the medium layer varies in a direction in such manner that the thickness of the medium layer at the center thereof is less than the thickness of the medium layer at both sides thereof, the improvement which comprises the electrophoresis performing in a direction perpendicular to the direction along which the thickness of the medium layer varies.

2. The process for electrophoresis of claim 1 wherein the medium layer has a constant thickness along said direction except at both sides.

3. The process for electrophoresis of claim 1 wherein the medium layer has a varying thickness having a curved surface.

4. In a rectangular means for electrophoresis comprising a support and an electrophoresis medium layer provided on the support, the improvement which comprises the thickness of the medium layer and thickness of the support both varying in the same direction in such a manner that the thickness of the medium layer at the center thereof is less than the thickness of the medium layer at both sides thereof and the thickness of the support at the center thereof is more than the thickness of the support at both sides thereof, said direction being perpendicular to a direction along which the electrophoresis is performed.

5. The means for electrophoresis of claim 4 wherein the medium layer has a constant thickness along said direction except at both sides and the support has a constant thickness along said direction except at both sides.

6. The means for electrophoresis of claim 4 wherein the medium layer has a varying thickness having a curved surface and the support has a varying thickness having a curved surface, the curved surface of the medium layer facing the curved surface of the support.

* * * * *